(12) United States Patent
Jongsma et al.

(10) Patent No.: US 7,208,164 B2
(45) Date of Patent: Apr. 24, 2007

(54) OVO IMMUNIZATION AGAINST INFECTIOUS BRONCHITIS

(75) Inventors: Berend Jongsma, Soest (NL); Frans Gerrit Davelaar, Putten (NL); Marinus Wynand Westrate, Weesp (NL)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/858,277

(22) Filed: Jun. 1, 2004

(65) Prior Publication Data

US 2004/0219171 A1 Nov. 4, 2004

Related U.S. Application Data

(63) Continuation of application No. 09/775,750, filed on Feb. 2, 2001, now abandoned.

(60) Provisional application No. 60/185,631, filed on Feb. 29, 2000.

(51) Int. Cl.
*A61K 39/205* (2006.01)
*A61K 39/12* (2006.01)
*A01N 3/00* (2006.01)

(52) U.S. Cl. .............. 424/224.1; 424/204.1; 424/93.1; 424/93.2

(58) Field of Classification Search ............ 424/9.2, 424/204.1, 222.1
See application file for complete search history.

(56) References Cited

U.S. PATENT DOCUMENTS 5,750,113 A 5/1998 Cook .................. 424/222.1

FOREIGN PATENT DOCUMENTS

WO WO 99/53950 10/1999

OTHER PUBLICATIONS

Chew et al., Avian Disease 41:598-603, 1997, Pathogenicity of Attenuated Infectious Bronchitis Virus for Oviducts of Chickens Exposed in Ovo.
Wakenell, et al., Am J Vet Res, vol. 47, No. 4, Apr. 1986, Chicken embryonal vaccination with avian infectious bronchitis virus.
Wakenell, et al., Avian Diseases 39:752-765, 1995, Embryo Vaccination of Chickens with Infectious Bronchitis Virus: Histologic and Ultrastructural Lesion Response and Immunologic Response to Vaccination.

*Primary Examiner*—Bruce R. Campell
*Assistant Examiner*—Bo Peng
(74) *Attorney, Agent, or Firm*—Frank R. Cottingham

(57) ABSTRACT

The present invention is directed to processes and compositions for protecting host animals (e.g., chickens) from exposure to virulent infectious bronchitis virus. In ovo administration of live, avirulent strains of IB at appropriate dosage levels on a per egg basis provides an effective and efficient vaccination having acceptable safety and efficacy features.

15 Claims, No Drawings

OVO IMMUNIZATION AGAINST INFECTIOUS BRONCHITIS

This application is a continuation of U.S. application Ser. No. 09/775,750, filed Feb. 2, 2001, now abandoned, claims the benefit under 35 U.S.C. §119(e) to a provisional application No. 60/185,631. filed on Feb. 29, 2000, the contents of each of which are hereby incorporated by reference in their entirety.

FIELD OF THE INVENTION

The invention is directed to novel ways of providing in ovo protection against infectious bronchitis (hereinafter, "IB") in host animals such as chickens. More particularly, vaccines derived from traditional commercially-available IB vaccines have proven to be both safe and efficacious upon appropriate in ovo administration to host animals as described herein.

BACKGROUND OF THE INVENTION

IB is a highly infectious/transmissible respiratory disease that affects chickens of all ages. The disease of IB is caused by a virus of the coronavirus group. IB disease symptoms vary widely; however, reported effects include death, respiratory tract distress, depressed production, decreased peak production of eggs, abnormalities in the eggshells, diarrhea, and a nephrosis/nephritis syndrome. Undesired weight loss in young chicks and/or insufficient/low-quality production of eggs from laying flocks are commercially-significant adverse impacts of IB disease in chickens.

Commercially-available vaccines for IB are not administered in ovo. Rather, they are administered post-hatch in a variety of formats. Briefly, such vaccines are typically administered by the labor-intensive methods of spraying (e.g., hand spray, knapsack spray, or automated spray equipment) or in drops (eye or nose).

As more fully explained below, the in ovo vaccines of the present invention provide distinctive advantages over the inconvenient and time-consuming post-hatch routes of administration presently available.

SUMMARY OF THE INVENTION

In brief, the present invention is directed to in ovo vaccines (hereinafter, "IOV") derived from commercially-available IB vaccines. Experimental results establish the safety and efficacy of the IOV relative to in ovo administration to chickens. Appropriate dosing parameters have also been developed. In addition to the IOV, the invention contemplates related compositions suitable for in ovo administration.

Processes for protecting a host animal against IB are also within the ambit of the present invention. Such administration provides economic advantages in that in ovo vaccination is easier, and faster and utilizes a smaller dose of vaccine than conventionally administered vaccines.

DETAILED DESCRIPTION OF THE INVENTION

The present invention is directed to in ovo inoculations of animals, in particular, poultry. As that term is used herein, poultry refers to any bird or fowl which is bred commercially, and therefore includes chickens, turkeys, ducks, geese, bantams, quail, pigeons and the like. Of particular interest are chickens.

All types of vaccines for inoculation are contemplated for use in the invention, and in particular, a vaccine against infectious bronchitis, or IB. The vaccines may be obtained from whatever source is available in the industry. A preferred vaccine is an IB vaccine marketed under the trademark POULVAC®, which is available from Fort Dodge Animal Health in Fort Dodge, Iowa or Weesp, the Netherlands. Other IB vaccines may also be utilized. The vaccines of the invention preferably contain live, nonvirulent strains of the infectious agent, including IB. The vaccines should induce an immunogenic response in the host, generating the production of antibodies sufficient to confer immunity.

The quantity of pathogenic agent to be included in the vaccine to be administered to the host egg can vary, depending upon the particular pathogenic agent, and also the size of the animal (larger animals may require larger quantities of agent). A desired quantity is within the range of about $10^{-1.0}$ $EID_{50}$ to about $10^{2.0}$ $EID_{50}$ of pathogenic agent, e.g. virus (in particular IB), per vaccine dose. A quantity within the range of about $10^{0.0}$ $EID_{50}$ to about $10^{1.0}$ $EID_{50}$ pathogenic agent per vaccine dose is also useful herein. Throughout this application, "$EID_{50}$" refers to a 50% egg infectious dose.

In addition to the foregoing, the vaccines may be formulated with known additives, including adjuvants. Examples of desirable adjuvants include polymers and copolymers of acrylic acid, as well as those derived from other alkyl esters. Other constituents include media such as water, saline solution, or water-in-oil emulsions in quantities sufficient to top off the dose. The pathogenic agent may be dissolved or suspended in the media just described. In a preferred embodiment of the invention, the vaccine is formulated with substantially no virus neutralizing factor.

A vaccine dose is typically within the range of about 0.001 mL to about 1.0 mL, and more preferably within the range of about 0.01 to 0.1 mL, with about 0.05 mL being even more preferred.

The dosing regimen for the vaccine most desirably includes administration in ovo to a developing chick in a fertilized egg that has not yet hatched. One administration of the dose is typically preferred, but more than one is within the scope of the invention. The dosing schedule chosen should ensure both the safety of the developing animal, as well as efficacy of immunization.

A dose of vaccine may be administered in ovo during a time period which is within the range of about day 1 up to and including about a few minutes before hatching. More preferably, a dose is delivered in ovo within the time period of about day 5 to about day 25. Even more desirably, the dose is administered during the period of about day 10 to about day 20. A dosing at about day 18 may be particularly desirable.

Administration of the vaccine may be done by hand, but is more typically and economically administered using commercially available egg injection equipment, such as that available from Embrex, Inc. of North Carolina.

An advantage of in ovo vaccine according to the invention is that the vaccine is applied to each individual bird (egg). This translates into better accuracy as compared with more traditional vaccination programs (non-in ovo). This is reflected in the high percentages of protection against challenge in the vaccinated birds. In addition, because the in ovo birds are vaccinated at a considerably earlier age than are those who receive the inoculation post-in ovo, there is more time for the birds to develop their immunity before exposure to outside ambient conditions in which virulent strains of the virus may be present. This result has been unexpected. Normally, introduction of live viruses into embryos would have been expected to generate fairly lethal results. A developing embryo is a highly fragile organism, and the presence of a live virus such as IB would have normally killed the developing animal. At best, much of the art has mandated the use of a virus neutralizing factor to prevent such an occurrence when chicks are inoculated in ovo. Conversely, introduction of what would have been considered exceedingly minute quantities of live virus, while not killing the embryo, would not have been expected to impart satisfactory immunogenic properties to the organism.

The following examples are provided by way of illustration, and should not be construed as limiting the scope of the invention.

A) THE VACCINE.

The IOV were prepared using a commercially-available IB vaccine (Poulvac® IB MM) from Fort Dodge Animal Health in Fort Dodge, Iowa or Weesp, The Netherlands by reconstitution with saline to a concentration of $10^{2.0}$, $10^{1.0}$, $10^{0.0}$ and $10^{-1.0}$ of IB/virus vaccine per dose (0.05 ml). Poulvac® IB MM contains infectious bronchitis virus strain 1263 of the Massachusetts serotype. This commercially-available IB vaccine has not been approved or indicated for in ovo administration.

B) EXAMPLE 1

Safety Study for in Ovo Chicken Vaccination

Specific-pathogen-free (hereinafter, "SPF") chicken eggs were commercially obtained from Charles River SPAFAS, Inc. [190 Route 165, Preston, Conn. 06365]. In brief, SPF eggs from SPAFAS were incubated within appropriate facilities. At 18 days of incubation, 4 groups of 25 eggs were administered in ovo vaccinations using graded doses of the IOV derived from the Poulvac® IB MM.

The IOV of the present invention were prepared as follows. A commercially-available IB vaccine (Poulvac® IB MM) from Fort Dodge Animal Health in Fort Dodge, Iowa or Weesp, The Netherlands was obtained. This vaccine contains live, attenuated IB virus in a freeze-dried environment. Prior to its use herein, this vaccine contained a titer of $10^{6.4}$ $EID_{50}$ IB virus per vial. Next, this vaccine was reconstituted in saline and then further admixed with saline until the following concentrations were obtained: solutions containing, respectively, titers of $10^{2.0}$, $10^{1.0}$, $10^{0.0}$, and $10^{-1.0}$ of IB virus/vaccine per dose (size: 0.05 ml) were prepared.

At 18 days of incubation, Groups 1–4 (each consisting of 25 eggs) were injected in ovo with a dose of 0.05 ml per egg of the vaccines of the present invention containing, respectively, the following titers of IB virus: titers of $10^{2.0}$, $10^{1.0}$, $10^{0.0}$, and $10^{-1.0}$ of IB virus/vaccine per dose. As a control, Group 5 (also consisting of 25 eggs) did not receive any in ovo injections at day 18 of incubation. To administer the injections, commercially-available equipment (Inovoject® egg injection machine) from Embrex, Inc. [P.O.B. 13989, Research Triangle Park, North Carolina 27709-3989] was used according to manufacturer's instructions.

Until hatching, both the inoculated eggs (i.e., 100 eggs total in Groups 1–4 @25 eggs/group) and the control eggs (i.e., 25 eggs in Group 5) were incubated within the same incubator. The number of hatched eggs per group was experimentally recorded at days 20, 21, and 22 of incubation.

Tables 1 and 2 presents the results obtained.

TABLE 1

Calculated Hatchability Results
Hatchability results after in ovo vaccination at incubation day 18 with a dose of 0.05 ml/egg of IB vaccine to Groups 1–5 (25 eggs/group)

| Group | $EID_{50}$ | # hatched | % hatched |
|---|---|---|---|
| 1 | $10^{2.0}$ | 17 | 72 |
| 2 | $10^{1.0}$ | 21 | 84 |
| 3 | $10^{0.0}$ | 17 | 72 |
| 4 | $10^{-1.0}$ | 20 | 80 |
| 5 | None | 24 | 96 |

TABLE 2

Raw Hatchability Results
Hatchability results after in ovo vaccination at incubation day 18 with a dose of 0.05 ml/egg of IB vaccine to Groups 1–5 (25 eggs/group)

| Group | $EID_{50}$ | # hatched (day 20) | # hatched (day 21) | # hatched (day 22) | total # hatched |
|---|---|---|---|---|---|
| 1 | $10^{2.0}$ | — | 12 | 5 | 17 |
| 2 | $10^{1.0}$ | — | 10 | 11 | 21 |
| 3 | $10^{0.0}$ | — | 12 | 5 | 17 |
| 4 | $10^{-1.0}$ | — | 17 | 3 | 20 |
| 5 | none | — | 24 | — | 24 |

Hatchability in the inoculated eggs ranged from 72% to 84% in comparison to 96% for the negative control eggs of Group 5. All of these observed hatchability percentages were within customary limits. No systemic effects between the inoculated groups (i.e., Groups 1–4) was observed.

Based upon the results of Experiment 1 as set forth above, it was concluded that in ovo vaccination at incubation day 18 using dosages ranging from a low of $10^{-1.0}$ $EID_{50}$ IB vaccine to a high of $10^{2.0}$ $EID_{50}$ IB vaccine was safe relative to hatchability.

C) EXAMPLE 2

Efficacy Study for in Ovo Vaccination of SPF Chicken Eggs

SPF chicken eggs were obtained from Charles River SPAFAS, Inc. All 200 eggs were incubated in appropriate facilities. At 18 days incubation, all eggs were candled; 14 eggs were unfertilized and within 20 eggs the embryos had died. The eggs were divided into 5 groups with 25 eggs/group.

The vaccine to be administered in ovo was prepared in accordance with the procedures of Example 1 above.

At 18 days of incubation, similar to the protocol used in Example 1 above, Groups 1–4 were injected in ovo with the following titers of $EID_{50}$ of IB vaccine/virus in a dose of 0.05 ml/egg: $10^{2.0}$, $10^{1.0}$, $10^{0.0}$, and $10^{-1.0}$. As a control, Group 5 eggs were not injected with any vaccines at incubation day 18.

Next, the inoculated and the control eggs were placed in separate incubators (without turning) for each group of eggs and were left to hatch in the isolation pen in which they were housed. The number of eggs hatched was experimentally recorded at days 20, 21, and 22 of incubation. At 22 days of incubation, all remaining eggs were removed from the incubators.

The chicks were housed in their respective isolation pens with positive air pressure. All chicks were kept on wood shavings. The rooms were provided with heater lamps to create local temperatures substantially above the room temperatures. Chicks were able to choose their preferred temperature by adjusting their distance from the heating lamp. All chicks were fed ad lib and drinking water was ad lib available in automatic drinkers. Within a week after hatching, all chicks were tagged with an identifying wing mark that contained both a color and a number. Chicks to be challenged (as described below) at 4 weeks of age were moved to 1 animal room operating with positive air pressure just before the challenge. Additionally, the chicks were experimentally observed for clinical signs of IB throughout the study.

Tables 3 and 4 present the hatchability results.

TABLE 3

Calculated Hatchability Results
hatchability results after in ovo vaccination at incubation day 18 with a dose of 0.05 ml/egg of IB vaccine to Groups 1–5 (25 eggs/group)

| Group | $EID_{50}$ | # hatched | % hatched |
|---|---|---|---|
| 1 | $10^{2.0}$ | 8 | 32 |
| 2 | 101.0 | 10 | 40 |
| 3 | $10^{0.0}$ | 11 | 44 |
| 4 | $10^{-1.0}$ | 14 | 56 |
| 5 | none | 20 | 80 |

TABLE 4

Raw Hatchability Results
hatchability results after in ovo vaccination at incubation day 18 with a dose of 0.05 ml/egg of IB vaccine to Groups 1–5 (25 eggs/group)

| Group | $EID_{50}$ | # hatched (day 20) | # hatched (day 21) | # hatched (day 22) | total # hatched |
|---|---|---|---|---|---|
| 1 | $10^{2.0}$ | — | 1 | 7 | 8 |
| 2 | $10^{1.0}$ | — | 2 | 8 | 10 |
| 3 | $10^{0.0}$ | — | 8 | 3 | 11 |
| 4 | $10^{-1.0}$ | — | 6 | 8 | 14 |
| 5 | none | — | 10 | 10 | 20 |

The observed hatchability was very low for all inoculated groups (it ranged from 32% to 56%) and decreased with increasing vaccine dose. In the control eggs of Group 5, 80% of the eggs hatched. It was concluded that, with respect to hatchability, the results obtained were not representative and were attributed to poor egg quality rather than to adverse effects of in ovo vaccinations with IB virus. As described in detail in Example 1, acceptable hatchability results were previously obtained.

An analysis of clinical signs (e.g., mortality) in non-challenged chicks further strengthened the above conclusion that the hatchability results were not representative. Table 5 below presents the mortality data for hatchlings/chicks from both the 4 vaccinated groups (i.e., Groups 1–4) and the 1 negative control group (i.e., Group 5). In Table 5, "PH" is an abbreviation for post-hatch. The observed clinical signs included the following results. Due to diarrhea, several chicks in all groups were in bad condition. Some chicks exhibited respiratory problems or umbilical hernia. A total of 5 chicks died (post-hatch) from yolk sac inflammation as follows: in Group 1, 1 chick died; in Group 2, 3 chicks died; and in group 4, 1 chick died. Post-hatch mortality results (including the deaths attributed to yolk sac inflammation) are presented in Table 5. For Group 1, 1 dead chick was not observed (which explains the finding at day 21 PH that 4 chicks in Group 1 were alive). In Group 5, 30% (i.e., 6 hatchlings/chicks) died shortly after hatching. At candling prior to in ovo vaccination, embryos in 10% of the eggs had died. These pre-inoculation deaths, in combination with the described mortality features of this study, established that inferior egg quality (rather than adverse effects attributable to the in ovo vaccinations) was responsible for both the hatchability results and the observed clinical signs prior to challenge.

TABLE 5

Clinical Signs In Non-Challenged Chicks
post-hatch (PH) mortality prior to challenge

| # days PH | Group 1 (n = 8) | Group 2 (n = 10) | Group 3 (n = 11) | Group 4 (n = 14) | Group 5 (n = 20) |
|---|---|---|---|---|---|
| 0 |  |  |  |  | 6 |
| 1 | 1 | 1 |  | 1 |  |
| 3 |  | 1 |  | 1 |  |
| 4 |  | 1 |  |  |  |
| 5 |  | 1 |  |  |  |
| 6 | 1 |  |  |  |  |
| # live chicks (day 21 PH) | 4 | 6 | 11 | 12 | 14 |

A challenge study was conducted as follows. In brief, virulent IB M41 virus was commercially-obtained from the Poultry Health Institute, Doorn, The Netherlands. This challenge virus had a titer of $10^{5.9}$ $EID_{50}$ per vial. A final solution containing $10^{4.5}$ $EID_{50}$ per ml of challenge virus was prepared by appropriate reconstitution with demineralized water and dilution with nutrient broth of 1 vial of the challenge virus.

At 4 weeks of age, all vaccinated and control chicks were challenged by administration of $10^{3.5}$ $EID_{50}$ in 0.1 ml (0.05 ocular and 0.05 intranasal) virulent IB M41 virus per chick. The chicks were evaluated using the cilia stopping test (hereinafter, "CST"). In brief, 6 days post-challenge (hereinafter, "PC"), the chicks were killed and their tracheas removed. One part per trachea was collected for microscopic examination and cillary activity was assessed. This assessment used the following scale: +=full movement; ±=impaired movement; and −=no movement. In cases of impairment, additional trachea parts were taken to confirm this finding. The percentage of protection against challenge with this virulent strain of IB was calculated using the following formula: protection %=(A+½B)(100)/C wherein A=# chicks assessed+; B=# chicks assessed±; and C=total # chicks.

Tables 6 and 7 presents the results of the challenge study.

TABLE 6

Calculated Results Of Post-Challenge Protection
Protection against challenge at 3 weeks of age with virulent IB virus as determined by CST

| Group ($EID_{50}$) | # chicks | protection % |
|---|---|---|
| 1 ($10^{2.0}$) | 4 | 100 |
| 2 ($10^{1.0}$) | 6 | 92 |
| 3 ($10^{0.0}$) | 11 | 100 |
| 4 ($10^{-1.0}$) | 12 | 100 |
| 5 (none) | 14 | 0 |

TABLE 7

Raw Results Of Post-Challenge Protection
Post-challenge assessments of protection with CST techniques

| Group (EID$_{50}$) | # chicks | +(full CST motion) | ±(impaired CST motion) | −(no CST motion) |
|---|---|---|---|---|
| 1 ($10^{2.0}$) | 4 | 4 | | |
| 2 ($10^{1.0}$) | 6 | 5 | 1 | |
| 3 ($10^{0.0}$) | 11 | 11 | | |
| 4 ($10^{-1.0}$) | 12 | 12 | | |
| 5 (none) | 14 | | | 14 |

As determined by the CST methodology, the protection afforded by in ovo vaccination at incubation day 18 with IB virus/vaccine derived from Poulvac®IB MM against exposure to a virulent challenge IB virus at 3 weeks of age was excellent. The protection percentages ranged from a low of 92% to a high of 100%.

In addition to the hatchability, clinical signs, and CST analyses discussed above, a serological study was also performed. In brief, blood samples were collected from the wing veins of all chicks up to a maximum number of 24 chicks per group at 3 weeks of age. Lacrimal fluid was collected after dropping 1 drop of glycerin into each eye from a maximum number of 5 chicks per group at 3 weeks of age. Antibody titers against the IB M41 antigen were measured in serum and lacrimal fluid using the HI test. The detection limit of the HI test corresponds with $^2$log HI titer=3.0. Geometric mean titers (hereinafter, "GMT") were calculated based upon the HI tests conducted. Tables 8 and 9 present the serological results.

TABLE 8

Calculated Serological Results
GMT against IB M41 antigen at 3 weeks of age using the HI test

| Group (EID$_{50}$) | serum (# chicks) | lacrimal fluid (# chicks) |
|---|---|---|
| 1 ($10^{2.0}$) | 3.0 (4) | 8.3 (3) |
| 2 ($10^{1.0}$) | 3.0 (6) | 7.5 (2) |
| 3 ($10^{0.0}$) | 3.1 (11) | 7.4 (5) |
| 4 ($10^{-1.0}$) | 3.1 (11) | 8.7 (3) |
| 5 (none) | 3.0 (14) | 9.7 (4) |

TABLE 9

Raw Serological Results
chicks with indicated $^2$log HI
titers against IB M41 antigen at 3 weeks of age

| Group (EID$_{50}$) | 0 |
|---|---|
| titer results based upon serum: | |
| 1 ($10^{2.0}$) | |
| 2 ($10^{1.0}$) | |
| 3 ($10^{0.0}$) | 0 |
| 4 ($10^{-1.0}$) | 0 |
| 5 (none) | 4 |
| titer results based upon lacrimal fluid | |
| 1 ($10^{2.0}$) | |
| 2 ($10^{1.0}$) | |
| 3 ($10^{0.0}$) | |
| 4 ($10^{-1.0}$) | |
| 5 (none) | |

In almost all chicks, antibody levels within the serum were not above the detection limit of $^2$log HI titer=3.0. Antibody titers in the lacrimal fluids of both the inoculated chicks and the control chicks were high. Accordingly, it is postulated that: (a) within the lacrimal fluids, the experimentally-determined antibody titers were non-specific; and (b) the glycerin used to collect the lacrimal fluids might have been responsible for this observed effect. No clear conclusions were drawn based upon these serological results discussed above.

Based upon the entirety of this Example 2 as described above, it was concluded that in ovo vaccination at day 18 of incubation of SPF chicken eggs with IB virus/vaccine at dosages of ranging from a low of $10^{-1.0}$ EID$_{50}$ per egg to a high of $10^{2.0}$ EID$_{50}$ per egg was efficacious in protecting chicks against exposure to a challenge at 3 weeks of age with virulent IB M41 virus.

D) EXAMPLE 3

Efficacy Study for in Ovo Vaccination of Commercial Chicken Eggs

Commercial chicken eggs for broilers were obtained from Pronk, Meppel, The Netherlands. These eggs were incubated within appropriate facilities. After 18 days incubation, all eggs were candled, and 4 groups of 28–30 eggs were inoculated with graded doses of the in ovo vaccine. The in ovo vaccines administered, hatching and/or husbandry conditions, the manner of egg injections, the preparation of the challenge virus, serological analysis, and the determination of protection using the CST methodology were all conducted as previously described above in Examples 1 and 2. Tables 10–16 below present the results from this study of in ovo vaccination with IB virus of commercial chicken eggs.

TABLE 10

Calculated Hatchability Results
hatchability results after in ovo vaccination
at incubation day 18 with a dose of 0.05 ml/egg
of IB vaccine to Groups 1–5 (28–30 eggs/group)

| Group | EID$_{50}$ | # hatched (total # eggs) | % hatched |
|---|---|---|---|
| 1 | $10^{2.0}$ | 25 (29) | 86 |
| 2 | $10^{1.0}$ | 26 (28) | 93 |
| 3 | $10^{0.0}$ | 25 (28) | 89 |
| 4 | $10^{-1.0}$ | 27 (30) | 90 |
| 5 | none | 24 (28) | 86 |

TABLE 11

Raw Hatchability Results
hatchability results after in ovo vaccination
at incubation day 18 with a dose of 0.05 ml/egg
of IB vaccine to Groups 1–5 (28–30 eggs/group)

| Group | EID$_{50}$ | # hatched (day 20) | # hatched (day 21) | # hatched (day 22) | total # hatched |
|---|---|---|---|---|---|
| 1 | $10^{2.0}$ | — | 22 | 3 | 25 |
| 2 | $10^{1.0}$ | 2 | 24 | — | 26 |
| 3 | $10^{0.0}$ | 18 | 7 | — | 25 |
| 4 | $10^{-1.0}$ | 18 | 9 | — | 27 |
| 5 | none | 13 | 11 | — | 24 |

As set forth above in Tables 10 and 11, hatchability in the inoculated groups (i.e., Groups 1–4) was good, within customary limits, and ranged from 86% to 93%. Hatchability in the control group (i.e., Group 5) was 86%.

TABLE 12

Clinical Signs In Non-Challenged Chicks
post-hatch (PH) mortality prior to challenge

| # days PH | Group 1 (n = 25) | Group 2 (n = 26) | Group 3 (n = 25) | Group 4 (n = 27) | Group 5 (n = 24) |
|---|---|---|---|---|---|
| 1 | 1 died | | | | 1 BC |
| 5 | 1 died (yolk sac) | | | | |
| 7 | | | | | 2 BC |
| 9 | | | | | 1 died |
|   | | | | | 1 killed |
| # live chicks (day 21 PH) | 23 | 26 | 25 | 27 | 22 |

Table 12 above sets forth the conditions and mortality of the chicks from Groups 1–5 prior to challenge with a virulent strain of IB virus. In Table 5, "BC" is used as an abbreviation for bad condition. To summarize the results: 2 chicks in Group 1 died (1 from yolk sac inflammation); and 2 control chicks from Group 5 were in bad condition (1 died on day 9 post-hatch and the other 1 chick was killed on day 9 post-hatch because it could not stand upright). Table 12 does not present clinical respiratory signs. Several chicks in groups given dosages of 100.0 or greater (i.e., Groups 1–3) showed mild respiratory signs probably due to IB virus replication from 6 days of age onward until challenge at 3 weeks of age (Groups 1 and 2) or until 12 days of age (Group 3). The observed respiratory signs were mild and no damage was seen at 6 days post-challenge as determined by the CST methodology (presented below).

Tables 13 and 14 presents the results of the challenge study.

TABLE 13

Calculated Results Of Post-challenge Protection
Protection against challenge at 3 weeks of age
with virulent IB virus as determined by CST

| Group ($EID_{50}$) | # chicks | protection % |
|---|---|---|
| 1 ($10^{2.0}$) | 23 | 100 |
| 2 ($10^{1.0}$) | 25 | 100 |
| 3 ($10^{0.0}$) | 25 | 96 |
| 4 ($10^{-1.0}$) | 27 | 89 |
| 5 (none) | 22 | 0 |

TABLE 14

Raw Results Of Post-Challenge Protection
post-challenge assessments of protection with CST techniques

| Group ($EID_{50}$) | # chicks | +(full CST motion) | ±(impaired CST motion) | −(no CST motion |
|---|---|---|---|---|
| 1 ($10^{2.0}$) | 23 | 23 | 0 | 0 |
| 2 ($10^{1.0}$) | 26 | 25 | 0 | 0 |
| 3 ($10^{0.0}$) | 25 | 23 | 2 | 0 |
| 4 ($10^{-1.0}$) | 27 | 23 | 2 | 2 |
| 5 (none) | 22 | 0 | 0 | 22 |

In Tables 13 and 14, 1 chick in Group 2 was in bad condition from the day after challenge until its death at 5 days post-challenge. This death was not attributed to either the in ovo vaccination or the subsequent challenge. As determined by the CST methodology, the protection afforded commercial eggs for broilers by in ovo vaccination at incubation day 18 with IB virus/vaccine derived from Poulvac® IB MM against exposure to a virulent challenge IB virus at 3 weeks of age was excellent. The protection percentages ranged from a low of 89% to a high of 100%. The control chicks (Group 5) had no protection against challenge with a virulent IB virus at 3 weeks of age.

Serological analysis yielded the results set forth below in Tables 15 and 16.

TABLE 15

Calculated Serological Results

| Group ($EID_{50}$) | GMT against IB M41 antigen at 3 weeks of age using the HI test of serum samples | # chicks |
|---|---|---|
| 1 ($10^{2.0}$) | 4.5 | 23 |
| 2 ($10^{1.0}$) | 4.0 | 22 |
| 3 ($10^{0.0}$) | 4.1 | 24 |
| 4 ($10^{-1.0}$) | 4.0 | 24 |
| 5 (none) | 3.8 | 22 |

TABLE 16

Raw Serological Results
chicks with indicated $^2$log HI
titers to IB M41 antigen at 3 weeks of age as
determined from serum

| Group ($EID_{50}$) | 3 | 4 | 5 | 6 | 7 |
|---|---|---|---|---|---|
| 1 ($10^{2.0}$) | 8 | 2 | 9 | 2 | 2 |
| 2 ($10^{1.0}$) | 11 | 3 | 5 | 3 | |
| 3 ($10^{0.0}$) | 8 | 7 | 7 | 2 | |
| 4 ($10^{-1.0}$) | 9 | 7 | 7 | 1 | |
| 5 (none) | 11 | 5 | 5 | 1 | |

As set forth above in Tables 15 and 16, serological analysis of serum samples revealed mean antibody titers in all inoculated groups were only slightly higher than those of the control chicks (i.e., Group 5). However, within the inoculated groups, the highest mean antibody titer was measured in Group 1 chicks; i.e., the chicks which had received the strongest dose of the in ovo vaccines. Additionally, in the vaccinated chicks, a considerable number showed antibody titers at or above the detection level.

Based upon the entirety of this Example 3 as described above, it was concluded that in ovo vaccination at day 18 of incubation of commercial chicken eggs for broilers with IB virus/vaccine at dosages of ranging from a low of $10^{-1.0}$ $EID_{50}$ per egg to a high of $10^{2.0}$ $EID_{50}$ per egg was efficacious in protecting chicks against exposure to a challenge at 3 weeks of age with virulent IB M41 virus.

Although the present invention has been described above in considerable detail, applicants desire the full extent of patent protection possible as defined and determined by the claims appended hereto, with reference to the above teachings but not limited to any specific example previously set forth.

What is claimed is:

1. A method of vaccinating a poultry animal against infectious bronchitis virus (IBV), said method comprising administering an IBV vaccine in ovo to a developing chick in a fertilized egg that has not yet hatched;

wherein said IBV vaccine comprises a solution comprising a live attenuated strain of IBV of $10^{-1.0}$ $EID_{50}$ to $10^{0.0}$ $EID_{50}$ per dose per egg;

wherein at least 80% of eggs receiving said vaccine hatch; and wherein at least 89% of chicks hatched from said eggs are protected against a challenge of virulent IBV administered to said chicks, and wherein the percent of chicks protected from said challenge is determined by a cilia stopping test (CST).

2. The method of claim 1, wherein 90% of eggs receiving said vaccine hatch.

3. The method of claim 1, wherein said vaccine comprises a solution comprising a live attenuated strain of IBV of $10^{-1.0}$ $EID_{50}$ per dose per egg.

4. The method of claim 1, wherein said vaccine comprises a solution comprising a live attenuated strain of IBV of $10^{0.0}$ $EID_{50}$ per dose per egg.

5. The method of claim 1, wherein said live attenuated strain of IBV is strain 1263 of the Massachusetts serotype.

6. The method of claim 1, wherein said IBV vaccine further comprises one or more adjuvant.

7. The method of claim 1, wherein said IBV vaccine contains no virus neutralizing factor.

8. The method of claim 1, wherein said IBV vaccine is administered in ovo at about day 5 to about day 25 of incubation.

9. The method of claim 8, wherein said IBV vaccine is administered in ovo at about day 10 to about day 20 of incubation.

10. The method of claim 9, wherein said IBV vaccine is administered in ovo at day 18 of incubation.

11. The method of claim 1, wherein said IBV vaccine is administered in ovo by hand.

12. The method of claim 1, wherein said IBV vaccine is administered mechanically using egg injection equipment.

13. The method of claim 1, wherein said IBV vaccine is administered in a volume of about 0.001 ml to about 1.0 ml of solution per dose.

14. The method of claim 13, wherein said IBV vaccine is administered in a volume of about 0.01 ml to about 0.1 ml of solution per dose.

15. The method of claim 14, wherein said IBV vaccine is administered in a volume of about 0.05 ml of solution per dose.

* * * * *